United States Patent [19]
Kikuchi et al.

[11] Patent Number: 5,847,187
[45] Date of Patent: Dec. 8, 1998

[54] ORGANIC PHOSPHOROUS COMPOUND, A PROCESS FOR PRODUCING THE SAME AND A USE THEREOF

[75] Inventors: Taketoshi Kikuchi, Osaka; Naoki Inui, Nara; Kanaku Fukuda, Osaka; Takashi Sanada, Chiba, all of Japan

[73] Assignee: Sumitomo Chemical Company, Limited, Osaka, Japan

[21] Appl. No.: 942,792

[22] Filed: Oct. 2, 1997

[30] Foreign Application Priority Data

Oct. 3, 1996 [JP] Japan ................................. 8-262889

[51] Int. Cl.$^6$ ........................................................ C07F 9/06
[52] U.S. Cl. ................................................ 558/171; 558/74
[58] Field of Search ......................... 558/74, 95, 96, 558/171

[56] References Cited

FOREIGN PATENT DOCUMENTS

05086084 A   4/1993   Japan .
08027172 A   1/1996   Japan .

OTHER PUBLICATIONS

CA:92:216156 abs of "Effect of antioxidants on the stability of ABS copolymers", Kirillova, Zh. Prikl Khim., 53(1), pp. 163–167, 1980.
CA:92:42763 abs of Stabilization of high–impact polystyrene, Kirillova, Zh Prikl. Khim., 52(9) pp. 2061–2065, 1979.

Primary Examiner—Paul J. Killos
Assistant Examiner—Jean F. Vollano
Attorney, Agent, or Firm—Pillsbury Madison & Sutro LLP

[57] ABSTRACT

An organic phosphorous compound represented by the following formula (I):

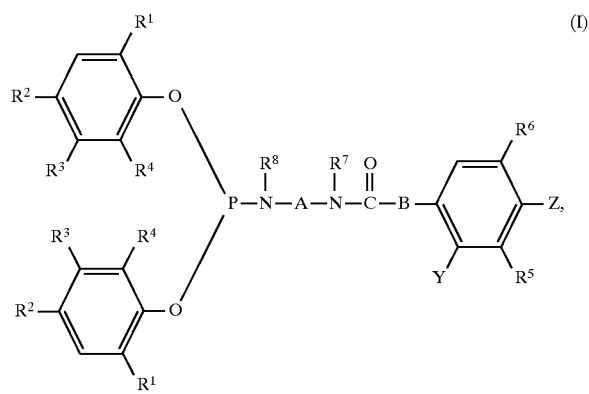

wherein $R^1$, $R^2$, $R^5$ and $R^6$ represent a hydrogen atom, an alkyl group, a cycloalkyl group, an alkylcycloalkyl group, an aralkyl group or a phenyl group; $R^3$ represents a hydrogen atom or an alkyl group; $R^4$ represents a hydrogen atom, an alkyl group, a cycloalkyl group, an alkylcycloalkyl group, an aralkyl group or a phenyl group, or the two $R^4$ may be combined with each other to form a direct bond, a sulfur bond (—S—), or aN optionally substituted methylene group; $R^7$ and $R^8$ represent a hydrogen atom or an alkyl group, or $R^7$ and $R^8$ may be combined with each other to form an alkylene group; A represents an alkylene group; B represents a direct bond or an alkylene group; and one of Y and Z represents a hydroxyl group, an alkoxy group or an aralkyloxy group, and the other one represents a hydrogen atom or an alkyl group; and the organic phosphorous compound is useful as a stabilizer for an organic material.

13 Claims, No Drawings

ORGANIC PHOSPHOROUS COMPOUND, A PROCESS FOR PRODUCING THE SAME AND A USE THEREOF

The present invention relates to a novel organic phosphorous compound, a process for producing the same and its use as a stabilizer for an organic material.

It has been known that organic materials such as thermoplastic resins, thermosetting resins, natural or synthetic rubbers, mineral oils, lubricating oils, adhesives and paints are deteriorated on their production, processing and use by an action of heat, oxygen, etc. As a result, their commercial value is drastically damaged with deterioration of physical strength of organic materials, change in flow properties, coloring, deterioration of surface properties, etc., which are caused by molecular scission and molecular crosslinking. It has hitherto been known that the organic materials are stabilized by containing various phenolic antioxidants and phosphorous antioxidants by preventing their heat deterioration and oxidation deterioration.

As the phosphorous antioxidant, for example, there is suggested a phosphorous compound having two N—P bonds in the molecule, such as N,N'-bis(2,4,8,10-tetra-t-butyl-dibenzo[d,f][1,3,2]dioxaphosphepin-6-yl)piperazine(JP-A-7-70158).

The present inventors have intensively studied about such phosphorous compounds. As a result, it has been found that a specific phosphorous compound wherein one of two N—P bonds is replaced by an N-carbonyl bond shows not only excellent color fastness but also excellent stabilizing effect. Thus, the present invention has been accomplished.

The present invention provides an organic phosphorous compound represented by the following formula (I):

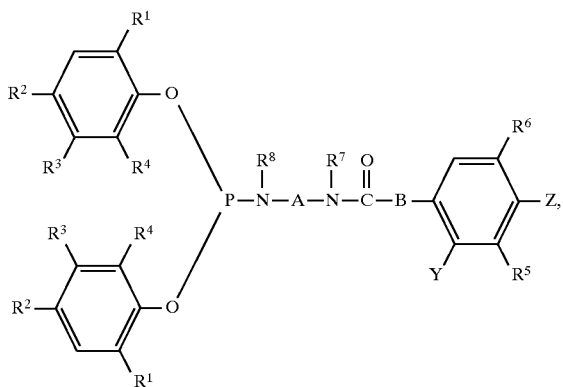

wherein $R^1$, $R^2$, $R^5$ and $R^6$ independently represent a hydrogen atom, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms or a phenyl group; $R^3$ represents a hydrogen atom or an alkyl group having 1 to 8 carbon atoms; $R^4$ represents a hydrogen atom, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms or a phenyl group, or the two $R^4$ may be combined with each other to form a direct bond, a sulfur bond (—S—), or a methylene group which is optionally substituted with alkyl having 1 to 8 carbon atoms or cycloalkyl having 5 to 8 carbon atoms; $R^7$ and $R^8$ independently represent a hydrogen atom or an alkyl group having 1 to 8 carbon atoms, or $R^7$ and $R^8$ may be combined with each other to form an alkylene group having 2 to 4 carbon atoms; A represents an alkylene group having 2 to 8 carbon atoms; B represents a direct bond or an alkylene group having 1 to 8 carbon atoms; and one of Y and Z represents a hydroxyl group, an alkoxy group having 1 to 8 carbon atoms or an aralkyloxy group having 7 to 12 carbon atoms, and the other one represents a hydrogen atom or an alkyl group having 1 to 8 carbon atoms.

The present invention also provides a process for producing the organic phosphorous compound represented by the formula (I).

The present invention further provides use of the organic phosphorous compound represented by the formula (I) as a stabilizer for an organic material.

In the organic phosphorous compound represented by the formula (I) of the present invention, the substituents $R^1$, $R^2$, $R^5$ and $R^6$ independently represent a hydrogen atom, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms or a phenyl group, preferably an alkyl group having 1 to 8 carbon atoms, a cycloalkyl group having 5 to 8 carbon atoms or an alkylcycloalkyl group having 6 to 12 carbon atoms.

Examples of the alkyl group having 1 to 8 carbon atoms as $R^1$, $R^2$, $R^5$ or $R^6$ include methyl, ethyl, n-propyl, i-propyl, n-butyl, i-butyl, sec-butyl, t-butyl, t-pentyl, i-octyl, t-octyl and 2-ethylhexyl.

Examples of the cycloalkyl group having 5 to 8 carbon atoms as $R^1$, $R^2$, $R^5$ or $R^6$ include cyclopentyl, cyclohexyl, cycloheptyl and cyclooctyl. Examples of the alkylcycloalkyl group having 6 to 12 carbon atoms as $R^1$, $R^2$, $R^5$ or $R^6$ include 1-methylcyclopentyl, 1-methylcyclohexyl and 1-methyl-4-i-propylcyclohexyl. Examples of the aralkyl group having 7 to 12 carbon atoms as $R^1$, $R^2$, $R^5$ or $R^6$ include benzyl, α-methylbenzyl and α, α-dimethylbenzyl.

It is more preferable that $R^1$ is a t-alkyl group such as t-butyl, t-pentyl and t-octyl. $R^2$ is more preferably an alkyl group having 1 to 5 carbon atoms, such as methyl, ethyl, n-propyl, i-propyl, n-butyl, i-butyl, sec-butyl, t-butyl and t-pentyl, particularly preferably methyl, t-butyl or t-pentyl.

$R^5$ is more preferably methyl, t-butyl, t-pentyl or t-octyl. $R^6$ is more preferably a hydrogen atom, methyl, t-butyl, t-pentyl or t-octyl.

The substituent $R^3$ represents a hydrogen atom or an alkyl group having 1 to 8 carbon atoms. Examples of the alkyl group having 1 to 8 carbon atoms as $R^3$ include methyl, ethyl, n-propyl, i-propyl, n-butyl, i-butyl, sec-butyl, t-butyl, t-pentyl, i-octyl, t-octyl and 2-ethylhexyl. $R^3$ is preferably a hydrogen atom or an alkyl group having 1 to 5 carbon atoms, particularly preferably a hydrogen atom or a methyl group.

$R^4$ represents a hydrogen atom, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms or a phenyl group, or the two $R^4$ may be combined with each other to form a direct bond, a sulfur bond(—S—), or a methylene group which is optionally substituted with alkyl having 1 to 8 carbon atoms or cycloalkyl having 5 to 8 carbon atoms.

Examples of the alkyl group having 1 to 8 carbon atoms as $R^4$ include methyl, ethyl, n-propyl, i-propyl, n-butyl, i-butyl, sec-butyl, t-butyl, t-pentyl, i-octyl, t-octyl and 2-ethylhexyl. Examples of the cycloalkyl group having 5 to 8 carbon atoms as $R^4$ include cyclopentyl, cyclohexyl, cycloheptyl and cyclooctyl. Examples of the alkylcycloalkyl group having 6 to 12 carbon atoms as $R^4$ include 1-methylcyclopentyl, 1-methylcyclohexyl and 1-methyl-4-i-propylcyclohexyl. Examples of the aralkyl group having 7 to 12 carbon atoms as $R^4$ include benzyl, α-methylbenzyl and α, α-dimethylbenzyl.

It is preferable that $R^4$ is a hydrogen atom, methyl or a t-alkyl group such as t-butyl, t-pentyl and t-octyl, or the two $R^4$ may be combined with each other to form a direct bond, a sulfur bond(—S—), an unsubstituted methylene group, and a methylene group substituted with methyl, ethyl, n-propyl, i-propyl, n-butyl, i-butyl and t-butyl.

$R^7$ and $R^8$ independently represent a hydrogen atom or an alkyl group having 1 to 8 carbon atoms, or $R^7$ and $R^8$ may be combined with each other to form an alkylene group having 2 to 4 carbon atoms. Examples of the alkyl group having 1 to 8 carbon atoms as $R^7$ or $R^8$ include methyl, ethyl, n-propyl, i-propyl, n-butyl, i-butyl, sec-butyl, t-butyl, t-pentyl, i-octyl, t-octyl and 2-ethylhexyl. Examples of the alkylene group having 2 to 4 carbon atoms as $R^7$ or $R^8$ include ethylene, propylene, butylene, 1-methylethylene and 1,2-dimethylethylene.

It is preferable that $R^7$ and $R^8$ are combined with each other to form an alkylene group having 2 to 4 carbon atoms. It is more preferable that they are combined together with "A" in the formula (I) and two N(s) to form a nitrogen-containing ring such as piperazine.

"A" in the formula (I) represents an alkylene group having 2 to 8 carbon atoms. Examples of the alkylene group as "A" include ethylene, propylene, butylene, pentamethylene, hexamethylene, octamethylene and 2,2-dimethyl-1,3-propylene. Preferably, it is ethylene or propylene.

"B" in the formula (I) represents a direct bond or an alkylene group having 1 to 8 carbon atoms. Examples of the alkylene group as "B" include methylene, ethylene, propylene, butylene, pentamethylene, hexamethylene, octamethylene and 2,2-dimethyl-1,3-propylene. Preferably, it is a direct bond, ethylene or the like.

One of Y and Z represents a hydroxyl group, an alkoxy group having 1 to 8 carbon atoms or an aralkyloxy group having 7 to 12 carbon atoms, and the other one represents a hydrogen atom or an alkyl group having 1 to 8 carbon atoms.

Examples of the alkyl group having 1 to 8 carbon atoms as Y or Z include methyl, ethyl, n-propyl, i-propyl, n-butyl, i-butyl, sec-butyl, t-butyl, t-pentyl, i-octyl, t-octyl and 2-ethylhexyl. Examples of the alkoxy group having 1 to 8 carbon atoms as Y or Z include an alkoxy group whose alkyl moiety is methyl, ethyl, n-propyl, i-propyl, n-butyl, i-butyl, sec-butyl, t-butyl, t-pentyl, i-octyl, t-octyl or 2-ethylhexyl. Examples of the aralkyloxy group having 7 to 12 carbon atoms as Y or Z include an aralkyloxy group whose aralkyl moiety is benzyl, α-methylbenzyl or α, α-dimethylbenzyl. One of Y and Z is preferably a hydroxyl group or a methoxy group.

The organic phosphorous compound represented by the above formula (I) can be produced, for example, by reacting a phenol or a bisphenol represented by the following formula (II):

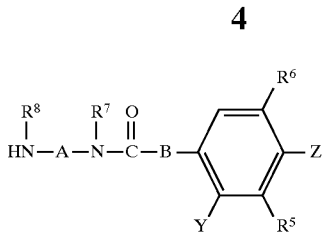

wherein $R^1$, $R^2$, $R^3$ and $R^4$ are as defined above, phosphorous trihalide and an amine compound represented by the following formula (III):

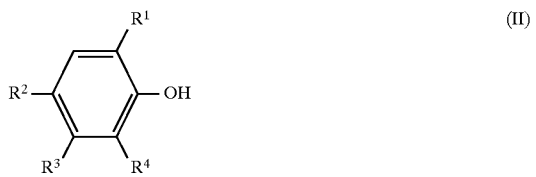

wherein $R^5$, $R^6$, $R^7$, $R^8$, A, B, Y and Z are as defined above.

Examples of the phosphorous trihalide used for the reaction include phosphorous trichloride and phosphorous tribromide. Among them, phosphorous trichloride is preferably used.

The reaction can be accelerated by coexistence of a dehydrohalogenating agent such as amines, pyridines, pyrrolidines and amides, or a hydroxide of an alkaline metal or an alkaline earth metal.

The amines usable for the reaction includes a primary amine, a secondary amine and a tertiary amine. Examples thereof include t-butylamine, t-pentylamine, t-hexylamine, t-octylamine, di-t-butylamine, di-t-pentylamine, di-t-hexylamine, di-t-octylamine, trimethylamine, triethylamine, N,N-dimethylaniline and N,N-diethylaniline. Among them, triethylamine is preferable.

Examples of the pyridines usable for the reaction include pyridine and picoline. Among them, pyridine is preferable. Examples of the pyrrolidines usable for the reaction include 1-methyl-2-pyrrolidine.

Examples of the amides usable for the reaction include N,N-dimethylformamide and N,N-dimethylacetamide. Among them, N,N-dimethylformamide is preferably used.

Examples of the hydroxide of the alkaline metal or alkaline earth metal usable for the reaction include sodium hydroxide and calcium hydroxide. Among them, sodium hydroxide is preferable.

The reaction for producing an organic phosphorous compound of formula (I) is normally conducted in an organic solvent. The organic solvent is not specifically limited unless the reaction is inhibited. Examples thereof include aromatic hydrocarbon, aliphatic hydrocarbon, oxygen-containing hydrocarbon and hydrogenated hydrocarbon.

Examples of the aromatic hydrocarbon include benzene, toluene, xylene and ethylbenzene. Examples of the aliphatic hydrocarbon include n-hexane, n-heptane and n-octane. Examples of the oxygen-containing hydrocarbon include diethyl ether, dibutyl ether, tetrahydrofuran and 1,4-dioxane. Examples of the halogenated hydrocarbon include chloroform, carbon tetrachloride, monochlorobenzene, dichloromethane, 1,2-dichloroethane and dichlorobenzene. Among them, toluene, xylene, n-hexane, n-heptane, diethyl ether, tetrahydrofuran, 1,4-dioxane, chloroform and dichloromethane are preferably used.

The reaction for producing the organic phosphorous compound of formula (I) may be conducted according to a so-called two-stage reaction method in which a phenol or bisphenol represented by the formula (II) is reacted with the phosphorous trihalide to form an intermediate firstly, and then the intermediate is reacted with the amine compound represented by the formula (III).

When a phenol is used as the starting compound in the two-stage reaction method, the phosphorous trihalide is preferably used in an amount of about 0.5 to 0.55 mols, more preferably about 0.5 to 0.52 mols, per mol of the phenol. When a bisphenol is used as the starting compound, the phosphorous trihalide is preferably used in an amount of about 1 to 1.1 mols, more preferably about 1 to 1.05 mols, per mol of the bisphenol. When a dehydrohalogenating agent is used in the reaction between a phenol or a bisphenol represented by the formula (III) with aphosphorous trihalide, it is preferably used in an amount of about 0.05 to 2.4 mols, more preferably about 2 to 2.1 mols, per mol of the phosphorous trihalide.

The reaction between a phenol or a bisphenol represented by the formula (II) with a phosphorous trihalide is normally carried out at about 0° to 200° C. It is considered that an intermediate halogenophosphite is produced by this reaction. The resulting reaction mixture is normally fed to the reaction with the amine compound (III) as it is, although the intermediate in the reaction mixture may be fed to the following reaction after isolation.

When using aphenol as the starting compound, the amine compound (III) is normally used in an amount of about 0.5 to 0.55 mols per mol of the phenol When using a bisphenol as the starting compound, the amine compound (III) is normally used in an amount of about 1 to 1.1 mols per mol of the bisphenol.

In this reaction with the amine compound (III), the dehydrohalogenating agent can also be used. When the dehydrohalogenating agent is used in the reaction with the amine compound (III), the amount of the dehydrohalogenating agent is preferably about 0.05 to 1.2 mols per mol of the amine compound (III). When using the excess dehydrohalogenating agent in the first reaction, the amount of the dehydrohalogenating agent in the reaction with the amine compound (III) is normally calculated by including amount of the residual dehydrohalogenating agent.

The reaction with the amine compound (III) is normally carried out at the temperature of about 0° to 200° C.

After completion of the reaction, when using the dehydrohalogenating agent, the organic phosphorous compound (I) of the present invention can be obtained by removing a halogenhalogenate of the dehydrohalogenating agent produced by the reaction, and then removing the solvent, followed by a suitable post treatment such as crystallization or column chromatography.

Examples of the phenol represented by the formula (II), as a starting material of the organic phosphorous compound (I), include 2-methylphenol, 4-methylphenol, 2,4-dimethylphenol, 2,6-dimethylphenol, 2,4,6-trimethylphenol, 2-ethylphenol, 4-ethylphenol, 2,4-diethylphenol, 2,6-diethylphenol, 2,4,6-triethylphenol, 2-t-butylphenol, 4-t-butylphenol, 2-t-butyl-4-methylphenol, 2-t-butyl-5-methylphenol, 2-t-butyl-4-ethylphenol, 2,4-di-t-butylphenol, 2-t-butyl-6-methylphenol, 2-t-butyl-6-ethylphenol, 2,6-di-t-butylphenol, 2,4-dimethyl-6-t-buthylphenol, 2,6-dimethyl-4-t-butylphenol, 2-methyl-4,6-di-t-butylphenol, 3-methyl-4,6-di-t-butylphenol, 2-ethyl-4,6-di-t-butylphenol, 3-ethyl-4,6-di-t-butylphenol, 4-methyl-2,6-di-t-butylphenol, 4-ethyl-2,6-di-t-butylphenol, 2,4,6-tri-t-butylphenol, 2,4-di-t-pentylphenol, 2-t-octylphenol, 2,4-di-t-octylphenol, 2,6-di-t-octylphenol, 2,4,6-tri-t-octylphenol, 2-nonylphenol, 4-nonylphenol, 2-cyclohexyl-4-methylphenol and 2-(1-methylcyclohexyl)-4-methylphenol.

Examples of the bisphenol represented by the formula (II) include 2,2'-methylenebis(4-methyl-6-t-butylphenol), 2,2'-methylenebis(4-ethyl-6-t-butylphenol), 2,2'-methylenebis(4-n-propyl-6-t-butylphenol), 2,2'-methylenebis(4-i-propyl-6-t-butylphenol), 2,2'-methylenebis(4-n-butyl-6-t-butylphenol), 2,2'-methylenebis(4-i-butyl-6-t-butylphenol), 2,2'-methylenebis(4,6-di-t-butylphenol), 2,2'-methylenebis(4-t-pentyl-6-t-butylphenol), 2,2'-methylenebis(4-nonyl-6-t-butylphenol), 2,2'-methylenebis(4-t-octyl-6-t-butylphenol), 2,2-methylenebis(4-methyl-6-t-pentylphenol), 2,2'-methylenebis(4-methyl-6-cyclohexylphenol), 2,2'-methylenebis[4-methyl-6-($\alpha$-methylcyclohexyl)phenol)], 2,2'-mnethylenebis(4-methyl-6-t-nonylphenol), 2,2'-methylenebis(4-methyl-6-t-octylphenol), 2,2'-methylenebis(4,6-di-t-pentylphenol), 2,2'-methylenebis[4-nonyl-6-($\alpha$-methylbenzyl)phenoll, 2,2'-methylenebis[4-nonyl-6-($\alpha,\alpha$-dimethylbenzyl)phenol], 2,2'-ethylidenebis(4-methyl-6-butylphenol), 2,2'-ethylidenebis(4-ethyl-6-t-butylphenol), 2,2'-ethylidenebis(4-n-propyl-6-t-butylphenol), 2,2'-ethylidenebis(4-i-propyl-6-t-butylphenol), 2,2'-ethylidenebis(4-n-butyl-6-t-butylphenol), 2,2'-ethylidenebis(4-i-butyl-6-t-butylphenol), 2,2'-ethylidenebis(4,6-di-t-butylphenol), 2,2'-ethylidenebis(4-t-pentyl-6-t-butylphenol), 2,2'-ethylidenebis(4-nonyl-6-t-butylphenol), 2,2'-ethylidenebis(4-t-octyl-6-t-butylphenol), 2,2'-ethylidenebis(4-methyl-6-t-pentylphenol), 2,2'-ethylidenebis(4-methyl-6-cyclohexylphenol), 2,2'-ethylidenebis[4-methyl-6-($\alpha$-methylcyclohexyl)phenol)], 2,2'-ethylidenebis(4-methyl-6-nonylphenol), 2,2'-ethylidenebis(4-methyl-6-t-octylphenol), 2,2'-ethylidenebis(4,6-di-t-pentylphenol), 2,2'-ethylidenebis[4-nonyl-6-($\alpha$-methylbenzyl)phenol], 2,2'-ethylidenebis[4-nonyl-6-($\alpha,\alpha$-dimethylbenzyl)phenol], 2,2'-propylidenebis(4-methyl-6-t-butylphenol), 2,2'-propylidenebis(4-ethyl-6-t-butylphenol), 2,2'-propylidenebis(4-n-propyl-6-t-butylphenol), 2,2'-propylidenebis(4-i-propyl-6-t-butylphenol), 2,2'-propylidenebis(4-n-butyl-6-t-butylphenol), 2,2'-propylidenebis(4-i-butyl-6-t-butylphenol) ) 2,2'-propylidenebis(4,6-di-t-butylphenol), 2,2'-propylidenebis(4-t-pentyl-6-t-butylphenol), 2,2'-propylidenebis(4-nonyl-6-t-butylphenol), 2,2'-propylidenebis (4-t-octyl-6-t-butylphenol), 2,2'-propylidenebis(4-methyl-6-t-pentylphenol), 2,2'-propylidenebis(4-methyl-6-cyclohexylphenol), 2,2'-propylidenebis[4-methyl-6-($\alpha$-methylcyclohexyl)phenol)], 2,2'-propylidenebis(4-methyl-6-nonylphenol), 2,2'-propylidenebis(4-methyl-6-t-octylphenol), 2,2'-propylidenebis(4,6-di-t-pentylphenol), 2,2'-propylidenebis[4-nonyl-6-($\alpha$-methylbenzyl)phenol], 2,2'-propylidenebis[4-nonyl-6-($\alpha,\alpha$-dimethylbenzyl)phenol], 2,2'-butylidenebis(4-methyl-6-t-butylphenol), 2,2'-butylidenebis(4-ethyl-6-t-butylphenol), 2,2'-butylidenebis(4,6-di-t-butylphenol), 2,2'-butylidenebis(4-methyl-6-cyclohexylphenol), 2,2'-butylidenebis[4-methyl-6-($\alpha$-methylcyclohexyl)phenol)], 2,2'-butylidenebis(4,6-di-t-pentylphenol), 2,2'-i-butylidenebis(4-methyl-6-t-butylphenol), 2,2'-i-butylidenebis(4-ethyl-6-t-butylphenol), 2,2'-i-butylidenebis(4,6-di-t-butylphenol), 2,2'-i-butylidenebis(4-methyl-6-cyclohexylphenol), 2,2'-i-butylidenebis[4-methyl-6-($\alpha$-methylcyclohexyl)phenol)], 2,2'-i-butylidenebis(4,6-di-t-pentylphenol), 2,2'-i-pentylidenebis(4-methyl-6-t-butylphenol), 2,2'-i-pentylidenebis(4-ethyl-6-t-butylphenol), 2,2'-i-pentylidenebis(4,6-di-t-butylphenol), 2,2'-i-pentylidenebis(4-methyl-6-cyclohexylphenol), 2,2'-pentylidenebis[4-methyl-6-($\alpha$-methylcyclohexy)phenol], 2,2'-pentylidenebis(4,6-di-t-pentylphenol), biphenyl-2,2'-diol, 3,3',5,5'-tetra-t-butylbiphenyl-2,2'-diol and 1,1'-binaphthyl-2,2'-diol.

The bisphenol of formula (II) can be produced by condensing an alkylphenol according to a known method described, for example, in JP-A-52-122350, U.S. Pat. No. 2,538,355 or JP-B-2-47451. An alkylphenol which are commercially available can also be used.

The amine compound of formula (III) as another starting material can be produced by reacting the corresponding carboxylic acid represented by the following formula (IV):

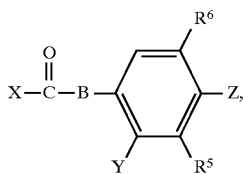

(IV)

wherein $R^5$, $R^6$, Y and Z are as defined above; and X represents a hydroxyl group, a lower alkoxy group or a halogen atom with a corresponding diamide represented by the following formula (VI):

$$R^8HN-A-NHR^7, \qquad (VI)$$

wherein $R^7$, $R^8$ and A are as defined above according to a normal method, if necessary, under the coexistence of dicyclocarbodiimide, N,N-carbonyldiimidazole, phosphorous oxychloride, titanium tetrachloride, lithium amide, dibutyltin oxide, dimethylaluminum amide and the like.

Examples of the amine compound of formula (III) include N-(3-t-butyl-2-hydroxybenzoyl)piperazine, N-(3-t-butyl-4-hydroxybenzoyl)piperazine, N-(3-t-butyl-2-hydroxy-5-methylbenzoyl)piperazine, N-(3,5-di-t-butyl-2-hydroxybenzoyl)piperazine, N-(3-t-butyl-4-hydroxy-5-methylbenzoyl)piperazine, N-(3,5-di-t-butyl-4-hydroxybenzoyl)piperazine, N-(2-methyl-3,5-di-t-butyl-4-hydroxybenzoyl)piperazine, N-(3-t-butyl-2-methoxybenzoyl)piperazine, N-(3-t-butyl-4-methoxybenzoyl)piperazine, N-(3-t-butyl-2-methoxy-5-methylbenzoyl)piperazine, 2-(3,5-di-t-butyl-2-methoxybenzoyl)piperazine, N-(3-t-butyl-4-methoxy-5-methylbenzoyl)piperazine, N-(3,5-di-t-butyl-4-methoxybenzoyl)piperazine, N-(2-methyl-3,5-di-t-butyl-4-methoxybenzoyl)piperazine, N-(3-t-butyl-2-hydroxyphenylacetyl)piperazine, N-(3-t-butyl-4-hydroxyphenylacetyl)piperazine, N-(3-t-butyl-2-hydroxy-5-methylphenylacetyl)piperazine, N-(3,5-di-t-butyl-2-hydroxyphenylacetyl)piperazine, N-(3-t-butyl-4-hydroxy-5-methylphenylacetyl)piperazine, N-(3,5-di-t-butyl-4-hydroxyphenylacetyl)piperazine, N-(2-methyl-3,5-di-t-butyl-4-hydroxyphenylacetyl)piperazine, N-(3-t-butyl-2-methoxyphenylacetyl)piperazine, N-(3-t-butyl-4-methoxylphenylacetyl)piperazine, N-(3-t-butyl-2-methoxy-5-methylphenylacetyl)piperazine, 2-(3,5-di-t-butyl-2-methoxyphenylacetyl)piperazine, N-(3-t-butyl-4-methoxy-5-methylphenylacetyl)piperazine, N-(3,5-di-t-butyl-4-methoxyphenylacetyl)piperazine, N-(2-methyl-3,5-di-t-butyl-4-methoxyphenylacetyl)piperazine, N-[3-(3-t-butyl-2-hydroxyphenyl)propionyl]piperazine, N-[3-(3-t-butyl-4-hydroxyphenyl)propionyl]piperazine, N-[3-(3-t-butyl-2-hydroxy-5-methylphenyl)propionyl]piperazine, N-[3-(3-t-butyl-2-hydroxy-5-methylphenyl)propionyl]piperazine, N-[3-(3,5-di-t-butyl-2-hydroxyphenyl)propionyl]piperazine, N-[3-(3-t-butyl-4-hydroxy-5-methylphenyl)propionylpiperazine, N-[3-(3,5-di-t-butyl-4-hydroxyphenyl)propionyl piperazine, N-[3-(2-methyl-3,5-di-t-butvl-4-hydroxyphenyl)propionyl]piperazine, N-[3-(3-t-butyl-2-methoxyphenyl)propionyl]piperazine, N-[3-(3-t-butyl-2-hydroxy-5-methylphenyl)propionyl]piperazine, N-[3-(3-t-butyl-2-methoxy-5-methylphenvl)propionyl]piperazine, 2-(3,5-di-t-butyl-2-methoxyphenyl)propionyl)piperazine, N-[3-(3-t-butyl-4-methoxy-5-methylphenyl)propionyl]piperazine, N-[3-(3,5-di-t-butyl-4-methoxyphenyl)propionyl]piperazine, N-[3-(2-methyl- 3,5-di-t-butyl-4-methoxyphenyl)propionyl]piperazine, N-(3-t-butyl-2-hydroxybenzoyl)ethylenediamine, N-(3-t-butyl-4-hydroxybenzoyl)ethylenediamine, N-(3-t-butyl-2-hydroxy-5-methylbenzoyl)ethylenediamine, N-(3,5-di-t-butyl-2-hydroxybenzoyl)ethylenediamine, N-(3-t-butyl-4-hydroxy-5-methylbenzoyl)ethylenediamine, N-(3,5-di-t-butyl-4-hydroxybenzoyl)ethylenediamine, N-(2-methyl-3,5-di-t-butyl-4-hydroxybenzoyl)ethylenediamine, N-(3-t-butyl-2-methoxybenzoyl)ethylenediamine, N-(3-t-butyl-4-methoxybenzoyl)ethylenediamine, N-(3-t-butyl-2-methoxy-5-methylbenzoyl)ethylenediamine, 2-(3,5-di-t-butyl-2-methoxybenzoyl)ethylenediamine, N-(3-t-butyl-4-methoxy-5-methylbenzoyl)ethylenediamine, N-(3,5-di-t-butyl-4-methoxybenzoyl)ethylenediamine, N-(2-methyl-3,5-di-t-butyl-4-methoxybenzoyl)ethylenediamine, N-(3-t-butyl-2-hydroxyphenylacetyl)ethylenediamine, N-(3-t-butyl-4-hydroxyphenylacetyl)ethylenediamine, N-(3-t-butyl-2-hydroxy-5-methylphenylacetyl)ethylenediamine, N-(3,5-di-t-butyl-2-hydroxyphenylacetyl)ethylenediamine, N-(3-t-butyl-4-hydroxy-5-methylphenylacetyl)ethylenediamine, N-(3,5-di-t-butyl-4-hydroxyphenylacetyl)ethylenediamine, N-(2-methyl-3,5-di-t-butyl-4-hydroxyphenylacetyl)ethylenediamine, N-(3-t-butyl-2-methoxyphenylacetyl)ethylenediamine, N-(3-t-butyl-4-methoxyphenylacetyl)ethylenediamine, N-(3-t-butyl-2-methoxy-5-methylphenylacetyl)ethylenediamine, 2-(3,5-di-t-butyl-2-methoxyphenylacetyl)ethylenediamine, N-(3-t-butyl-4-methoxy-5 -methylphenylacetyl)ethylenediamine, N-(3,5-di-t-butyl-4-methoxyphenylacetyl)ethylenediamine, N-(2-methyl-3,5-di-t-butyl-4-methoxyphenylacetyl) ethylenediamine, N-[3-(3-t-butyl-2-hydroxyphenyl) propionyl]ethylenediamine, N-[3-(3-t-butyl-4-hydroxyphenyl)propionyl]ethylenediamine, N-(3-(3-t-butyl-2-hydroxy-5-methylphenyl)propionyl] ethylenediamine, N-[3-(3,5-di-t-butyl-2-hydroxyphenyl) propionyl]ethylenediamine, N-[3-(3-t-butyl-4-hydroxy-5-methylphenyl)propionyl]ethylenediamine, N-[3-(3,5-di-t-butyl-4-hydroxyphenyl)propionyl]ethylenediamine, N-[3-(2-methyl-3,5-di-t-butyl-4-hydroxyphenyl)propionyl] ethylenediamine, N-[3-(3-t-butyl-2-methoxyphenyl) propionyl]ethylenediamine, N-[3-(3-t-butyl-4-methoxyphenyl)propionyl]ethylenediamine, N-[3-(3-t-butyl-2-methoxy-5-methylphenyl)propionyl] ethylenediamine, 2-(3,5-di-t-butyl-2-methoxyphenyl) propionyl]ethylenediamine, N-r[3-(3-t-butyl-4-methoxy-5-methylphenyl)propionyl]ethylenediamine, N-[3-(3,5-di-t-butyl-4-methoxyphenyl)propionyl]ethylenediamine, N-[3-(2-methyl-3,5-di-t-butyl-4-methoxyphenyl)propionyl] ethylenediamine, N-[3-(3-t-butyl-2-hydroxybenzoyl)-N,N'-dimethylethylenediamine, N-[3-(3-t-butyl-4-hydroxybenzoyl)-N,N'-dimethylethylenediamine, N-[3-(3-t-butyl-2-hydroxy-5-methvlbenzoyl)-N,N'-dimethylethylenediamine, N-(3,5-di-t-butyl-2-hydroxybenzoyl)-N,N'-dimethylethylenediamine, N-(3-t-butyl-4-hydroxy-5-methylbenzoyl)-N,N'-dimethylethylenediamine, N-(3,5-di-t-butyl-4-hydroxybenzoyl)-N,N'-dimethylethylenediamine, N-(2-methyl-3,5-di-t-butyl-4-hydroxybenzoyl)-N,N'-dimethylethylenediamine, N-(3-t-butyl-2-hydroxybenzoyl)-N,N'-dimethylethylenediamine, N-(3-t-butyl-4-methoxybenzoyl)-N,N'-dimethylethylenediamine, N-(3-t-butyl-2-methoxy-5-methylbenzoyl)-N,N'-dimethylethylenediamine, 2-(3,5-di-t-butyl-2-methoxybenzoyl)-N,N'-dimethylethylenediamine, N-(3-t-butyl-4-methoxy-5-methylbenzoyl)-N,N'-dimethylethylenediamine, N-(3,5-di-t-butyl-4-methoxybenzoyl)-N,N'-dimethylethylenediamine, N-(2-methyl-3,5-di-t-butyl-4-methoxybenzoyl)-N,N'-dimethylethylenediamine, N-(3-t-butyl-2-hydroxyphenylacetyl)-N,N'-dimethylethylenediamine, N-(3-t-butyl-4-hydroxyphenylacetyl)-N,N'- dimethylethylenediamine, N-(3-t-butyl-2-hydroxy-5-methylphenylacetyl)-N,N'-dimethylethylenediamine, N-(3,5-di-t-butyl-2-hydroxyphenylacetyl)-N,N'-dimethylethylenediamine, N-(3-t-butyl-4-hydroxy-5-methylphenylacetyl)-N,N'-dimethylethylenediamine, N-(3,5-di-t-butyl-4-hydroxyphenylacetyl)-N,N'-dimethylethylenediamine, N-(2-methyl-3,5-di-t-butyl-4-hydroxyphenylacetyl)-N,N'-dimethylethylenediamine, N-(3-t-butyl-2-methoxyphenylacetyl)-N,N'-dimethyiethylenediamine, N-(3-t-butyl-4-methoxyphenylacetyl)-N,N'-dimethylethylenediamine, N-(3-t-butyl-2-methoxy-5-methylphenylacetyl)-N,N'-dimethylethylenediamine, N-(3,5-di-t-butyl-2-methoxyphenylacetyl)-N,N'-dimethylethylenediamine, N-(3-t-butyl-4-methoxy-5-methylphenylacetyl)-N,N'-dimethylethylenediamine, N-(3,5-di-t-butyl-4-methoxyphenylacetyl)-N,N'-dimethylethylenediamine, N-(2-methyl-3,5-di-t-butyl-4-methoxyphenylacetyl)-N,N'-dimethylethylenediamine, N-[3-(3-t-butyl-2-hydroxyphenyl)propionyl]-N,N'-dimethylethylenediamine, N-r3-(3-t-butyl-4-hydroxyphenyl)propionyl]-N,N'-dimethylethylenediamine, N-[3-(3-t-butyl-2-hydroxy-5-methylphenyl)propionyl]-N,N'-dimethylethylenediamine, N-[3-(3,5-di-t-butyl-2-hydroxyphenyl)propionyl]-N,N'-dimethylethylenediamine, N-[3-(3-t-butyl-4-hydroxy-5-methylphenyl)propionyl]-N,N'-dimethylethylenediamine, N-[3-(3,5-di-t-butyl-4-hydroxyphenyl)propionyl]-N,N'-dimethylethylenediamine, N-[3-(2-methyl-3,5-di-t-butyl-4-hydroxyphenyl)propionyl]-N,N'-dimethylethylenediamine, N-[3-(3-t-butyl-2-methoxyphenyl)propionyl]-N,N'-dimethylethylenediamine, N-[3-(3-t-butyl-4-methoxyphenyl)propionyl]-N,N'-dimethylethylenediamine, N-[3-(3-t-butyl-2-methoxy-5-methylphenyl)propionyl]-N,N'-dimethylethylenediamine, 2-3,5-di-t-butyl-2-methoxyphenyl)propionyl]-N,N'-dimethylethylenediamine, N-3-(3-t-butyl-4-methoxy-5-methylphenyl)propionyl]-N,N'-dimethylethylenediamine, N-[3-(3,5-di-t-butyl-4-methoxyphenyl)propionyl]-N,N'-dimethylethylenediamine, N-[3-(2-methyl-3,5-di-t-butyl-4-methoxyphenyl)propionyl]-N,N'-dimethylethylenediamine, N-(3-t-butyl-2-hydroxybenzoyl)propylenediamine, N-(3-t-butyl-4-hydroxybenzoyl)propylenediamine, N-(3-t-butyl-2-hydroxy-5-methylbenzoyl)propylenediamine, N-(3,5-di-t-butyl-2-hydroxybenzoyl)propylenediamine, N-(3-t-butyl-4-hydroxy-5-methylbenzoyl)propylenediamine, N-(3,5-di-t-butyl-4-hydroxybenzoyl)propylenediamine, N-(2-methyl-3,5-di-t-butyl-4-hydroxybenzoyl)propylenediamine, N-(3-t-butyl-4-methoxybenzoyl)propylenediamine, N-(3-t-butyl-2-methoxy-5-methylbenzoyl)propylenediamine, 2-(3,5-di-t-butyl-2-methoxybenzoyl)propylenediamine, N-(3-t-butyl-4-methoxy-5-methylbenzoyl)propylenediamine, N-(3,5-di-t-butyl-4-methoxybenzoyl)propylenediamine, N-(2-methyl-3,5-di-t-butyl-4-methoxybenzoyl)propylenediamine, N-(3-t-butyl-2-hydroxyphenylacetyl)propylenediamine, N-(3-t-butyl-4-hydroxyphenylacetyl)propylenediamine, N-(3-t-butyl-2-hydroxy-5-methylphenylacetyl)propylenediamine, N-(3,5-di-t-butyl-2-hydroxyphenylacetyl)propylenediamine, N-(3-t-butyl-4-hydroxy-5-methylphenylacetyl)propylenediamine, N-(3,5-di-t-butyl-4-hydroxyphenylacetyl)propylenediamine, N-(2-methyl-3,5-di-t-butyl-4-hydroxyphenylacetyl)propylenediamine, N-(3-t-butyl-2-methoxyphenylacetyl)propylenediamine, N-(3-t-butyl-4-hydroxyphenylacetyl)propylenediamine, N-(3-t-butyl-2-methoxy-5-methylphenylacetyl)propylenediamine, N-(3,5-di-t-butyl-2-methylphenylacetyl)propylenediamine, N-(3-t-butyl-4-methoxy-5-methylphenylacetyl)propylenediamine, N-(3,5-di-t-butyl-4-methoxyphenylacetyl)propylenediamine, N-(2-methyl-3,5-di-t-butyl-4-methoxyphenylacetyl)propylenediamine, N-[3-(3-t-butyl-2-hydroxyphenyl)propionyl]propylenediamine, N-[3-(3-t-butyl-4-hydroxyphenyl)propionyl]propylenediamine, N-[3-(3-t-butyl-2-hydroxy-5-methylphenyl)propionyl]propylenediamine, N-[3-(3,5-di-t-butyl-2-hydroxyphenyl)propionyl]propylenediamine, N-[3-(3-t-butyl-4-hydroxy-5-methylphenyl)propionyl]propylenediamine, N-[3-(3,5-di-t-butyl-4-hydroxyphenyl)propionyl]propylenediamine, N-[3-(2-methyl-3,5-di-t-butyl-4-hydroxyphenyl)propionyl]propylenediamine, N-[3-(3-t-butyl-2-methoxyphenyl)propionyl]propylenediamine, N-[3-(3-t-butyl-4-methoxyphenyl)propionyl]propylenediamine, N-[3-(3-t-butyl-2-methoxy-5-methylphenyl)propionyl]propylenediamine, 2-(3,5-di-t-butyl-2-methoxyphenyl)propionyl]propylenediamine, N-[3-(3-t-butyl-4-methoxy-5-methylphenyl)propionyl]propylenediamine, N-[3-(3,5-di-t-butyl-4-methoxyphenyl)propionyl]propylenediamine and N-[3-(2-methyl-3,5-di-t-butyl-4-methoxyphenyl)propionyl]propylenediamine.

The hydrolysis resistance of the organic phosphorous compounds (I) of the present invention can be improved by containing an amine, an acid-bonded metal salt and the like.

Examples of the amine include trialkanolamines such as triethanolamine, tripropanolamine, tri-i-propanolamine and the like; dialkanolamines such as diethanolamine, dipropanolamine, di-i-propanolamine, tetraethanolethylenediamine, tetra-i-propanolethylenediamine and the like; monoalkanolamines such as dibutylethanolamine, dibutyl-i-propanolamine and the like; aromatic amines such as 1,3,5-trimethyl-2,4,6-triazine and the like; alkylamines such as dibutylamine, piperidine, 2,2,6,6,-tetramethylpiperidine, 4-hydroxy-2,2,6,6-tetramethylpiperidine and the like; polyalkylenepolyamines such as hexamethylenetetramine, triethylenediamine, triethylenetetramine, tetraethylenepentamine and the like; and hindered amine photostabilizers described hereinafter.

Furthermore, there can also be used a long-chain aliphatic amine described in JP-A-61-63686, a compound having a steric hindrance amine group described in JP-A-6-329830, a hindered piperidinyl photostabilizer described in JP-A-7-90270 and an organic amine described in JP-A-7-278164.

A proportion of the amine to be used is normally about 0.01 to 25% by weight based on the organic phosphorous compounds (I).

Typical examples of the acid-bonded metal salt include hydrotalcites. Examples of the hydrotalcites include double salt compounds represented by the following formula:

$$M^{2+}_{1-x} \cdot M^{3+}_{x} \cdot (OH^-)_2 \cdot (A^{n-})_{x/n} \cdot pH_2O$$

wherein $M^{2+}$ represents Mg, Ca, Sr, Ba, Zn, Pb, Sn and/or Ni; $M^{3+}$ represents Al, B or Bi; n represents a numerical value of 1 to 4; x represents a number of 0 to 0.5; p represents a number of 0 to 2; and $A^{n-}$ represents an anion having a valency of n.

Specific examples of the amino having a valence of n represented by $A^{n-}$ include $OH^-$, $Cl^-$, $Br^-$, $I^-$, $ClO_4^-$, $HCO_3^-$, $C_6H_5COO^-$, $CO_3^{2-}$, $SO^{2-}$, —OOCCOO—, $(CHOHCO)_2^{2-}$, $C_2H_4(COO)_2^{2-}$, $(CH_2COO)_2^{2-}$, $CH_3CHOHCOO—$, $SiO_3^{2-}$, $SiO_4^{4-}$, $Fe(CN)_6^{4-}$, $BO_3^{3-}$, $PO_3^{b\,3-}$ and $HPO_4^{2-}$.

Particularly preferred double salt compounds represented by the above formula include hydrotalcites represented by the following formula:

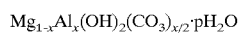

wherein x and p are as defined above.

The hydrotalcites may be natural or synthetic products, and can be used regardless of crystal structure and crystal particle diameter thereof.

Furthermore, an ultrafine zinc oxide described in JP-A-6-329830 and an inorganic compound described in JP-A-7-278164 can also be used.

A proportion of the acid-bonded metal salt to be used is normally about 0.01 to 25% by weight based on the organic phosphorous compounds (I).

The organic phosphorous compounds (I) of the present invention are effective for stabilizing an organic material against heat deterioration and oxidization deterioration. Examples of the organic material which can be stabilized by organic phosphorous compounds (I) of the present invention include the following:

(1) polyethylene, for example, high-density polyethylene (HD-PE), low-density polyethylene (LD-PE) and linear low-density polyethylene (LLDPE)
(2) polypropylene
(3) methylpentene polymer
(4) EEA (ethylene/ethyl acrylate copolymer) resin
(5) ethylene/vinyl acetate copolymer resin
(6) polystyrenes, for example, polystyrene, poly(p-methylstyrene) and poly($\alpha$-methylstyrene)
(7) As (acrylonitrile/styrene copolymer) resin
(8) ABS (acrylonitrile/butadiene/styrene copolymer) resin
(9) AAS (special acrylic rubber/acrylonitrile/styrene copolymer) resin
(10) ACS (acrylonitrile/chlorinated polyethylene/styrene copolymer) resin
(11) chlorinated polyethylene, polychloroprene, chlorinated rubber
(12) polyvinyl chloride, polyvinylidene chloride
(13) methacrylic resin
(14, etyhylene/vinyl alcohol copolymer resin
(15) fluororesin
(16) polyacetal
(17) grafted polyphenylene ether resin and polyphenylene sulfide resin
(18) polyurethane
(19) polyamide
(20) polyester resin, for example, polyethylene terephthalate and polybutylene terephthalate
(21) polycarbonate
(22) polyacrylate
(23) polysulfone, polyether ether ketone, polyether sulfone
(24) thermoplastic resin such as aromatic polyester resin, etc.
(25) epoxy resin
(26) diallyl phthalate prepolymer
(27) silicone resin
(28) unsaturated polyester resin
(29) acrylic-modified benzoguanamine resin
(30) benzoguanamine/melamine resin
(31) thermosetting resin such as urea resin, etc.
(32) polybutadiene
(33) 1,2-polybutadiene
(34) polyisoprene
(35) styrene/butadiene copolymer
(36) butadiene/acrylonitrile copolymer
(37) ethylene/propylene copolymer
(38) silicone rubber
(39) epichlorohydrin rubber
(40) acrylic rubber
(41) natural rubber
(42) chlorinated rubber paint
(43) polyester resin paint
(44) urethane resin paint
(45) epoxy resin paint
(46) acrylic resin paint
(47) vinyl resin paint
(48) aminoalkyd resin paint
(49) alkyd resin
(50) nitrocellulose resin paint
(51) oil-based paint
(52) wax, and
(53) lubricating oil.

The organic materials can be stabilized alone or in combination thereof. The organic materials which can be stabilized by organic phosphorous compounds (I) of the present invention are not limited to the organic materials exemplified above. Among them, the thermoplastic resin, particularly polyolefin such as polyethylene (e.g. HD—PE, 1D—PE, LIDPE, etc.) and polyolefin (e.g. polypropylene, etc.), and the engineering resin such as polvamide, polyethylene terephthalate, polybutylene terephthalate and polycarbonare, are more suitable to be stabilized by organic phosphorous compounds (I) of the present invention.

The polyolefins are not specifically limited. For example, they may be those obtained by the radical polymerization or those produced by the polymerization using a catalyst containing a metal of Group IVb, Vb, VIb or VIII of the periodic table. The catalyst containing such a metal may be a metal complex which is coordinated by one or more ligands, for example, oxide which is coordinated by a $\pi$ or $\sigma$ bond, halogenated compound, alcolate, ester, aryl and the like, and these complexes maybe used as it is, or a base material such as magnesium chloride, titanium chloride, alumina, silicon oxide, etc. may carry the complexes.

As the polyolefin, for example, there are preferably used those produced by using Ziegler-Natta catalyst, TNZ catalyst, metallocene catalyst, Phillips catalyst and the like.

Also the engineering resin is not specifically limited. The polyamide resin may be those which have an amide bond at the polymer chain and can be molten with heating. For example, they may be produced by any method such as condensation reaction between diamines and dicarboxylic acids, condensation reaction of aminocarboxylic acids and ring opening polymerization of lactams. Typical examples thereof include nylon 66, nylon 69, nylon 610, nylon 612, poly-bis(p-aminocyclohexyl)methanedodecamide, nylon 46, nylon 6, nylon 12 and copolymers (e.g. nylon 66/6 as a copolymer of nylon 66 and nylon 6, nylon 6/12, etc.).

The polyester resin may be those which have an ester bond at the polymer chain and can be molten with heating. Examples thereof include polyester obtained by the polycondensation between dicarboxylic acids and a dihydroxy compound. The polyester may be a homopolyester or a copolyester.

The polycarbonate may be those which have a carbonate bond at the polymer chain and can be molten with heating. Examples thereof include polycarbonate obtained by reacting an aromatic hydroxy compound and/or a small amount of polyhydroxy compound with a carbonate precursor such as phosgene, diphenyl carbonate, etc. in the presence of a solvent, an acid receptor and a molecular weight adjustor. The polycarbonate resin may be straight-chain or branched resin, or may be a copolymer.

When the organic material is stabilized by containing the organic phosphorous compounds (I) of the present invention, the organic phosphorous compounds (I) are normally formulated in an amount of about 0. 01 to 5 parts by weight, preferably about 0. 03 to 3 parts by weight, more preferably about 0.05 to 1 parts by weight, based on 100 parts by weight of the organic material. When the amount is less than 0.01 parts by weight, the stabilizing effect is not sufficient, necessarily. On the other hand, even when the amount exceeds 5 parts by weight, the improvement of the effect corresponding to the amount is not obtained and it is economically disadvantageous.

When the organic phosphorous compounds (I) of the present invention are contained in the organic material, if necessary, there can also be contained other additives such as phenol antioxidant, sulfur antioxidant, phosphorous antioxidant, ultraviolet absorber, photostabilizer, peroxide scavenger, polyamide stabilizer, hydroxylamine, lubricant, plasticizer, flame retardant, nucleating agent, metal inactivating agent, antistatic agent, pigment, filler, pigment, antiblocking agent, surfactant, processing aid, foaming agent, emulsifier, brightener, calcium stearate, neutralizing agent (e.g. hydrotalcite, etc.), coloring modifier (e.g. 9,10-dihydro-oxa-10-phosphophenanthrene-10-oxide, etc.) and co-stabilizer (e.g. benzofurans, indolines, etc. described in U.S. Pat. Nos. 4,325,853, 4,338,244, 5,175,312, 5,216,053, 5,252,643 and 4,316,611, DE-A-4,316,622 and 4,316,876, and EP-A-589,839 and 591,101). These additives can be formulated together with the organic phosphorous compounds (I), and also be formulated in the stage other than the stage where the organic phosphorous compounds (I) are formulated.

Examples of the phenol antioxidant include the followings.

(1) Examples of Alkylated Monophenol 2,6-di-t-butyl-4-methylphenol, 2,4,6-tri-t-butylphenol, 2,6-di-t-butyl-4-butylphenol, 2-t-butyl-4,6-dimethylphenol, 2,6-di-t-butyl-4-ethylphenol, 2,6-di-t-butyl-4-n-butylphenol, 2,6-di-t-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-t-butyl-4-methoxymethylphenol, 2,6-di-nonyl-4-methylphenol, 2,4-dimethyl-6-(1'-methylundecyl-1'-yl)phenol, 2,4-dimethyl-6'-(1'-methylheptadecyl-1'-yl)phenol, 2,4-dimethyl-6-(1'-methyltridecyl-1'-yl)phenol and a mixture thereof.

(2) Examples of Alkylthiomethylphenol 2,4-dioctylthiomethyl-6-t-butylphenol, 2,4-dioctylthiomethyl-6-methylphenol, 2,4-dioctylthiomethyl-6-ethylphenol, 2,6-didodecylthiomethyl-4-nonylphenol and a mixture thereof (3) Examples of Hydroquinone and Alkylated Hydroquinone 2,6-di-t-butyl-4-methoxyphenol, 2,5-di-t-butylhydroquinone, 2,5-di-t-amylhydroquinone, 2,6-diphenyl-4-octadecyloxyphenol, 2,6-di-t-butylhydroquinone, 2,5-di-t-butyl-4-hydroxyanisole, 3,5-di-t-butyl-4-hydroxyphenyl stearate, bis(3,5-di-t-butyl-4-hydroxyphenyl)adipate and a miture thereof (4) Examples of Tocopherol α-tocopherol, β-tocopherol, γ-tocopherol, δ-tocopherol and a mixture thereof (5) Examples of Hydroxylated Thiodiphenyl Ether 2,2'-thiobis(6-t-butylphenol), 2,2'-thiobis(4-methyl-6-t-butylphenol), 2,2'-thiobis(4-octylphenol), 4,4'-thiobis(3-methyl-6-t-butylphenol), 4,4'-thiobis(2-methyl-6-t-butylphenol), 4,4'-thiobis(3,6-di-t-amylphenol), 4,4'-(2,6-dimethyl-4-hydroxyphenyl)disulfide and the like (6) Examples of Alkylidenebisphenol and Derivative Thereof 2,2'-methylenebis(4-methyl-6-t-butylphenol), 2,2'-methylenebis(4-ethyl-6-t-butylphenol), 2,2'-methylenebis[4-methyl-6-(α-methylcyclohexyl)phenol)], 2,2'-methylenebis(4-methyl-6-cyclohexylphenol), 2,2'-methylenebis(4-methyl-6-nonylphenol), 2,2'-methylenebis(4,6-di-t-butylphenol)], 2,2'-ethylidenebis(4,6-di-t-butylphenol), 2,2'-ethylidenebis(4-isobutyl-6-t-butylphenol), 2,2'-methylenebis[6-(α-methylbenzyl)-4-nonylphenol], 2,2'-methylenebis[6-(α,α-dimethylbenzyl)-4-nonylphenol), 4,4'-methylenebis(6-t-butyl-2-methylphenol), 4,4'-methylenebis(2,6-di-t-butylphenol), 4,4'-butylidenebis(3-methyl-6-t-butylphenol), 1,1-bis(4-hydroxyphenyl)cyclohexane, 1,1-bis(5-t-butyl-4-hydroxy-2-methylphenyl)butane, 2,6-bis[3-t-butyl-5-methyl-2-hydroxybenzyl)-4-methylphenol, 1,1,3-tris(5-t-butyl-4-hydroxy-2-methylphenyl)butane, 1,1-bis(5-t-butyl-4-hydroxy-2-methylphenyl)-3-n-dodecylmercaptobutane, bis[3,3-bis-3'-t-butyl-4'-hydroxyphenyl)butyrate], bis(3-t-butyl-4-hydroxy-5-methylphenyl)dicyclopentadiene, bis[2-(3'-t-butyl-2'-hydroxy-5'-methylbenzyl)-6-t-butyl-4-methylphenyl]terephthalate, 1,1-bis(3,5-dimethyl-2-hydroxyphenyl)butane, 2,2-bis(3,5-di-t-butyl-4-hydroxyphenyl)propane, 2,2-bis(5-t-butyl-4-hydroxy-2-methylphenyl)-4-n-dodecylmercaptobutane, 1,1,5,5-tetra(5-t-butyl-4-hydroxy-2-methylphenyl)pentane, 2-t-butyl-6-(3'-t-butyl-5'-methyl-2'-hydroxybenzyl)-4-methylphenyl acrylate, 2,4-di-t-pentyl-6-[1-(2-hydroxy-3,5-di-t-pentylphenyl)ethyl]phenyl acrylate and a mixture thereof.

(7) Examples of O—, N— and S-Benzyl Derivative 3,5,3',5'-tetra-t-butyl-4,4'-dihydroxydibenzyl ether, octadodecyl-4-hydroxy-3,5-dimethylbenzylmercapto acetate, tris(3,5-di-t-butyl-4-hydroxybenzyl)amine, bis(4-t-butyl-3-hydroxy-2,6-dimethylbenzyl)dithioterephthalate, bis(3,5-di-t-butyl-4-hydroxybenzyl)sulfide, isooctyl-3,5-di-t-butyl-4-hydroxybenzylmercapto acetate and a mixture thereof (8) Examples of Hydroxybenzylated Malonate Derivative dioctadecyl-2,2-bis(3,5-di-t-butyl-2-hydroxybenzyl)malonate, dioctadecyl-2-(3-t-butyl-4-hydroxy-5-methylbenzyl)malonate, didodecylmercaptoethyl-2,2-bis(3,5-di-t-butyl-4-hydroxybenzyl)malonate, bis[4-(1,1,3,3-tetramethylbutyl)phenyl]-2,2-bis(3,5-di-t-butyl-4-hydroxybenzyl)malonate and a mixture thereof (9) Examples of Aromatic Hydroxybenzyl Derivative 1,3,5-trimethyl-2,4,6-tris(3,5-di-t-butyl-4-hydroxybenzyl)benzene, 1,4-bis(3,5-di-t-butyl-4-hydroxybenzyl)-2,3,5,6-tetramethylbenzene, 2,4,6-tris(3,5-t-butyl-4-hydroxybenzyl)phenol and a mixture thereof

(10) Examples of Triazine Derivative 2,4-bis(n-octylthio)-6-(4-hydroxy-3,5 -di-t-butylanilino)-1,3,5-triazine, 2-n-octylthio-4,6-bis(4-hydroxy-3,5-di-t-butylanilino)-1,3,5-triazine, 2-n-octylthio-4,6-bis(4-hydroxy-3,5-di-t-butylphenoxy)-1,3,5-triazine, 2,4,6-tris(3,5-di-t-butyl-4-hydroxy)-1,3,5-triazine, tris(4-t-butyl-3-hydroxy-2,6-dimethylbenzyl isocyanurate, tris(3,5-di-t-butyl-4-hydroxybenzyl)isocyanurate, 2,4,6-tris(3,5-di---butyl-4-hydroxyphenylethyl)-1,3,5-triazine, 2,4,6-tris(3,5-di-t-butyl-4-hydroxyphenylpropyl)-1,3,5-triazine, tris(3,5-dicyclohexyl-4-hydroxybenzyl)isocyanurate, tris[2-(3',5'-dit-butyl-4'-hydroxycinnamoyloxy)ethyl]isocyanurate and a mixture thereof

(11) Examples of Benzyl Phosphonate Derivative dimethyl-3,5-di-t-butyl-4-hydroxybenzyl phosphonate, diethyl-3,5-di-t-butyl-4-hydroxybenzyl phosphonate, dioctadecyl-3,5-di-t-butyl-4-hydroxybenzyl phosphonate, dioctadecyl-5-t-butyl-4-hydroxy-3-methylbenzyl phosphonate, calcium salt of 3,5-di-t-butyl-4-hydroxybenzyl phosphonic acid monoester and a mixture thereof

(12) Examples of Acylaminophenol Derivative anilide 4-hydroxylaurate, anilide 4-hydroxystearate, octyl-N-(3,5-di-t-butyl-4-hydroxyphenyl)carbanate and a mixture thereof

(13) Ester of β-(3,5-di-t-butyl-4-hydroxyphenyl) Propionic Acid and the Following Monohydric or Polyhydric Alcohol:

methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glvcol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2,2,2]octane and a mixture thereof

(14) Ester of β-(5-t-butyl-4-hydroxy-3-methylphenyl) Propionic Acid and the Following Monohydric or Polyhydric Alcohol:

methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2,2,2]octane and a mixture thereof

(15) Ester of β-(3,5-dicyclohexyl-4-hydroxyphenyl) Propionic Acid and the Following Monohydric or Polyhydric Alcohol:

methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2,2,2]octane and a mixture thereof

(16) Ester of 3,5-t-butyl-4-hydroxyphenylacetic Acid and the Following Monohydric or Polyhydric Alcohol:

methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2,2,2]octane and a mixture thereof

(17) Examples of amide of β-(3,5-di-t-butyl-4-hydroxyphenyl)Propionic Acid and the Following Amine:

N,N'-bis[3-(3',5'-di-t-butyl-4'-hydroxyphenyl)propionyl] hydrazine, N,N'-bis[3-(3',5'-di-t-butyl-4'-hydroxyphenyl)propionyl]hexamethylenediamine, N,N'-bis[3-(3',5'-di-t-butyl-4'-hydroxyphenyl) propionyl] trimethylenediamine and a mixture thereof Examples of the Sulfur Antioxidant Include the Followings:

dilauryl 3,3'-thiodipropionate, tridecyl 3,3'-thiodipropionate, dimyristyl 3,3'-thiodipropionate, distearyl 3,3'-thiodipropionate, lauryl stearyl 3,3'-thiodipropionate and neopentanetetraylkis(3-lauryl thiopropionate).

Examples of the Phosphorous Antioxidant Include the Followings:

triphenyl phosphite, tris(nonylphenyl)phosphite, tris(2,4-di-t-butylphenyl)phosphite, trilauryl phosphite, trioctadecyl phosphite, distearyl pentaerythritol diphosphite, diisodecyl pentaerythritol diphosphite, bis(2,4-di-t-butylphenyl)pentaerythritol diphosphite, bis(2,4-di-t-butyl-6-methylphenyl)pentaerythritol diphosphite, bis(2,4-di-t-butyl-6-methylphenyl)pentaerythritol diphosphite, bis(2,6-di-t-butyl-4-methylphenyl) pentaerythritol diphosphite, bis(2,4,6-tri-t-butylphenyl) pentaerythritol diphosphate, tristearyl sorbitol triphosphite, tetrakis(2,4-di-t-butylphenyl)-4,4'-diphenylene diphosphite, 2,2'-methylenebis(4,6-di-t-butylphenyl)2-ethylhexyl phosphite, 2,2'-ethylidenebis (4,6-di-t-butylphenyl)fluoro phosphite, bis(2,4-di-t-butyl-6-methylphenyl)ethyl phosphite, bis(2,4-di-t-butyl-6-methylphenyl)methyl phosphite, (2,4,6-tri-t-butylphenyl)-5-ethyl-5-butyl-1,3,2-oxaphosphorinane, 2,2',2''-nitrilo[triethyl-tris(3,3',5,5'-tetra-t-butyl-1,1'-biphenyl-2,2'-diyl)phosphite and a mixture thereof Examples of the Ultraviolet Absorber Include the Followings:

(1) Examples of Salicylate Derivative phenyl salicylate, 4-t-butylphenyl salicylate, 2,4-di-t-butylphenyl 3',5'-di-t-butyl-4'-hydroxybenzoate, 4-t-octylphenyl salicylate, bis(4-t-butylbenzoyl)resorcinol, benzoylresorcinol, hexadecyl 3',5'-di-t-butyl-4'-hydroxybenzoate, octadecyl 3',5'-di-t-butyl-4'-hydroxybenzoate, 2-methyl-4,6-di-t-butylphenyl 3',5'-di-t-butyl-4'-hydroxybenzoate and a mixture thereof (2) Examples of 2-hydroxybenzophenone Derivative 2,4-dihydroxybenzophenone, 2-hydroxy-4-methoxybenzophenone, 2-hydroxy-4-octoxybenzophenone, 2,2'-dihydroxy-4-methoxybenzophenone, bis(5-benzoyl-4-hydroxy-2-methoxyphenyl)methane, 2,2',4,4'-tetrahydroxybenzophenone and a mixture thereof (3) Examples of 2-(2'-hydroxyphenyl)benzotriazole 2-(2-hydroxy-5-methylphenyl)benzotriazole, 2-(3',5'-di-t-butyl-2'-hydroxyphenyl)benzotriazole, 2-(5'-t-butyl-2'-hydroxyphenyl)benzotriazole, 2-(2'-hydroxy-5'-t-octylphenyl)benzotriazole, 2-(3-t-butyl-2-hydroxv-5-methylphenyl)-5-chlorobenzotriazole, 2-(3'-s-butyl-2'-hydroxy-5'-t-butylphenyl)benzotriazole, 2-(2'-hydroxy-4'-octyloxypheny)benzotriazole, 2-(3',5'-di-t-amyl-2'-hydroxyphenyl)benzotriazole, 2-[2'-hydroxy-3',5'-bis(α,α-dimethylbenzyl)phenyl]-2H-benzotriazole, 2-[(3'-t-butyl-2'-hydroxyphenyl)-5'-(2-octyloxycarbonylethyl)phenyl]-5-chlorobenzotriazole, 2-[3'-t-butyl-5'-[2-(2-ethylhexyloxy) carbonylethyl]-2'-hydroxyphenyl]-5-chlorobenzotriazole, 2-[3'-t-butyl-2'hydroxy-5'-(2-methoxycarbonylethyl) phenyl]-5-chlorobenzotriazole, 2-[3'-t-butyl-2'-hydroxy-5'-(2-methoxycarbonylethyl)phenyl]benzotriazole, 2-[3'-t-butyl-2'-hydroxy-5-(2-octyloxycarbonylethyl)phenyl] benzotriazole, 2-[3'-t-butyl-2'-hydroxy-5'-[2-(2-ethylhexyloxy)carbonylethyl] phenyl]benzotriazole, 2-[2-hydroxy-3-(3,4,5,6-tetrahydrophthalimidemethyl)-5- methylphenyl]benzotriazole, 2-(3',5'-di-t-butyl-2-hydroxyphenyl)-5-chlorobenzotriazole, mixture of 2-(3'-dodecyl-2'-hydroxy-5'-methylphenyl)benzotriazole and 2-[3'-t-butyl-2'-hydroxy-5'-(2-isooctyloxycarbonylethyl)phenyl]benzotriazole, 2,2'-methylenebis[6-(2H-benzotriazol-2-yl)-4-(1,1,3,3-tetramethylbutyl)phenol, 2,2'-methylenebis[4-t-butyl-6-(2H-benzotriazol-2-yl)phenol], condensate of poly(3–11)(ethylene glycol) and 2-[3'-t-butyl-2'-hydroxy-5'-(2-methoxycarbonylethyl)phenyl] benzotriazole, condensate of poly(3–11)(ethylene glycol) and methyl 3-[3-(2H-benzotriazol-2-yl)-5-t-butyl-4-hydroxyphenyl]propionate, 2-ethylhexyl 3-[3-t-butyl-5-(5-chloro-2H-benzotriazol-2-yl)-4-hydroxyphenyl]propionate, octyl 3-[3-t-butyl-5-(5-chloro-2H-benzotriazol-2-yl)-4-hydroxyphenyl]propionate, methyl 3-[3-t-butyl-5-(5-chloro-2H-benzotriazol-2-yl)-4-hydroxyphenyl]propionate, 3-[3-t-butyl-5-(5-chloro-2H-benzotriazol-2-yl)-4-hydroxyphenyl] propionic acid and a mixture thereof.

Examples of the Photostabilizer Include the Followings.

(1) Examples of Hindered Amine Photostabilizer bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(N-octoxy-2,2,6,6-tetramethyl-4-piperidyl)sebacate, bis(N-benzyloxy-2,2,6,6-tetramethyl-4-piperidyl)sebacate, bis(N-cyclohexyloxy-2,2,6,6-tetramethyl-4-piperidyl)sebacate, bis(1,2,2,6,6-pentamethyl-4-piperidyl) 2-(3,5-di-t-butyl-4-hydroxybenzyl)-2-butylmalonate, bis(1-acrolyl-2,2,6,6-tetramethyl-4-piperidyl) 2,2-bis(3,5-di-t-butyl-4-hydroxybenzyl)-2-butylmalonate, bis(1,2,2,6,6-penatmethyl-4-piperidyl decanedioate, 2,2,6,6 -tetramethyl-4-piperidyl methacrylate, 4-[3-(3,5-di-t-butyl-4-hydroxyphenyl)propionyloxy]-1-[2-(3-(3,5-di-t-butyl-4-hydroxyphenyl)propionyloxy)ethyl]-2,2,6,6-tetramethylpiperidine, 2-methyl-2-(2,2,6,6-tetramethyl-4-piperidyl)amino-N-(2,2,6,6-tetramethyl-4-piperidyl) propionamide, tetarkis(2,2,6,6-tetramethyl-4-piperidyl) 1,2,3,4-butaneteracarboxylate, tetrakis(1,2,2,6,6-pentamethyl-4-piperidyl) 1,2,3,4-butanetetracarboxylate, mixed esterified product of 1,2,3,4-butanetetracarboxylic acid and 1,2,2,6,6-pentamethyl-4-piperidinol and 1-tridecanol, mixed esterified product of 1,2,3,4-butanetetracarboxylic acid and 2,2,6,6-tetramethyl-4-piperidinol and 1-tridecanol, mixed esterified product of 1,2,3,4-butanetetracarboxylic acid and 1,2,2,6,6-pentamethyl-4-piperidinol and 3,9-bis(2-hydroxy-1,1-dimethylethyl)-2,4,8,10-tetraoxaspiro[5.5]undecane, mixed esterified product of 1,2,3,4-butanetetracarboxylic acid and 2,2,6,6-tetarmethyl-4-piperidinol and 3,9-bis(2-hydroxy-1,1-dimethylethyl)-2,4,8,10-tetraoxaspiro[5.5]undecane, polycondensate of dimethyl succinate and 1-(2-hydroxyethyl)-4-hydroxy-2,2,6,6-tetramethylpiperidine, poly[(6-morpholino-1,3,5-triazin-2,4-diyl)((2,2,6,6-tetramethyl-4-piperidyl)imino)hexamethylene ((2,2,6,6-tetramethyl-4-piperidyl)imino)], poly[(6-(1,1,3,3-tetramethylbutyl)imino-1,3,5-triazin-2,4-diyl ((2,2,6,6-tetramethyl-4-piperidyl)imino)hexamethylene ((2,2,6,6-tetramethyl-4-piperidyl)imino)], polycondensate of N,N'-bis(2,2,6,6-tetramethyl-4-piperidyl)hexamethylenediamine and 1,2 -bromoethane, N,N',4,7-tetrakis[4,6-bis(N-butyl-N-(2,2,6,6-tetramethyl-4-piperidyl)amino)-1,3,5-triazin-2-yl]-4,7-diazadecane-1,10 diamine, N,N',4-tetra-4,6-bis(N-butyl-N-(2,2,6,6-tetramethyl-4-piperidyl)amino)-1,3,5-triazin-2-yl]-4,7-diazadecane-1,10 diamine, N,N',4,7-tetrakis[4,6-bis(N-butyl-N-(1,2,2,6,6-pentamethyl-4-piperidyl)amino)-1,3,5-triazin-2-yl]-4,7-diazadecane-1,10 diamine, N,N',4-tris[4,6-bis(N-butyl-N-(1,2,2,6,6-pentamethyl-4-piperidyl)amino)-1,3,5-triazin-2-yl]-4,7-diazadecane-1,10 diamine and a mixture thereof (2) Examples of Acrylate Photostabilizer ethyl α-cyano-β,β-diphenylacrylate, isooctyl α-cyano-β,β-diphenylacrylate, methyl β-carbomethoxycinnamate, methyl α-cyano-β-methyl-methoxycinnamate, butyl α-cyano-β-methyl-p-methoxycinnamate, methyl α-carbomethoxy-p-methoxycinnamate and N-(β-carbomethoxy-β-cyano-vinyl) -2-methylindoline and a mixture thereof (3) Examples of Nickel Photostabilizer nickel complex of 2,2'-thiobis-[4-(1,1,3,3-tetramethylbutyl)phenol], nickel dibutyldithiocarbamate, nickel salt of monoalkyl ester, nickel complex of ketoxime and a mixture thereof (4) Examples of Oxamide Photostabilizer 4,4'-dioctyloxyoxanilide, 2,2'-diethoxyoxanilide, 2,2'-dioctyloxy-5,5'-di-t-butylanilide, 2,2'-didodecyloxy-5,5'-di-t-butylanilide, 2-ethoxy-2'-ethyloxanilide, N,N'-bis(3-dimethylaminopropyl)oxamide, 2-ethoxy-5-t-butyl-2'-ethoxyanilide, 2-ethoxy-5,4'-di-t-butyl-2 '-ethyloxanilide and a mixture thereof (5) Examples of 2-(2-hydroxyphenyl)-1,3,5-triazine Photostabilizer 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(4-methylphenyl)-1,3,5-triazine, 2-[2-hydroxy-4-(2-hydroxy-3-butyloxypropoxy)phenyl]-4,6-bis(2,4-dimethylphenyl)-1,3,5-triazine, 2-[2-hydroxy-4-(2-hydroxy-3-octyloxyphenyl)-4,6-bis(2,4-dimethylphenyl)-1,3,5-triazine and a mixture thereof.

Examples of the Metal Inactivating Agent Include the Followings:

N,N'-diphenyloxamide, N-salicylal-N'-salicyloylhydrazine, N,N'-bis(salicyloyl)hydrazine, N,N'-bis(3,5-di-t-butyl-4-hydroxyphenylpropionyl) hydrazine, 3-salicyloylamino-1,2,4-triazole, bis (benzylidene)oxalyl dihydrazide, oxalinide, isophthaloyl dihydrazide, sebacoylbisphenyl hydrazide, N,N'-bis(salicyloyl)thiopropionyl dihydrazide and a mixture thereof Examples of the peroxide scavenger include ester of β-thiodipropionic acid, mercaptobenzoimidazole, zinc salt of 2-mercaptobenzoimidazole, zinc salt of dibutyldithiocarbamic acid, dioctadecyl disulfide, pentaerythritol tetrakis(β-dodecylmercapto)propionate and a mixture thereof.

Examples of the polyamide stabilizer include copper or divalent manganese salt of iodide or phosphorous compound and a mixture thereof.

Examples of the hydroxyamine include N,N-dibenzylhydroxyamine, N,N-diethylhydroxyamine, N,N-dioctylhydroxyamine, N,N-dilaurylhydroxyamine, N,N-ditetradecylhydroxyamine, N,N-dihexadecylhydroxyamine, N,N-dioctadecylhydroxyamine, N,N-dibenzylhydroxyamine, N,N-dibenzylhydroxyamine, N-hexadecyl-N-octadecylhydroxyamine, N-heptadecyl-N-octadecylhydroxyamine and a mixture thereof.

Examples of the neutralizing agent include calcium stearate, zinc stearate, magnesium stearate, hydrotalcite (basic magnesium aluminum hydroxycarbonate hydride), melamine, amine, polyamide, polyurethane and a mixture thereof.

Examples of the lubricant include aliphatic hydrocarbon (e.g. paraffin, wax, etc.), higher aliphatic acid having 8 to 22 carbon atoms, higher aliphatic acid (having 8 to 22 carbon atoms) metal (Al, Ca, Mg, Zn) salt, aliphatic alcohol having 8 to 22 carbon atoms, polyglycol, ester of higher fatty acid having 4 to 22 carbon atoms and aliphatic monohydric alcohol having 4 to 18 carbon atoms, higher aliphatic amide having 8 to 22 carbon atoms, silicone oil, rosin derivative and the like.

Examples of the Nucleating Agent Include the Followings:

sodium2,2'-methylenebis(4,6-di-t-butylphenyl) phosphate, [phosphoric acid-2,2'-methylenebis(4,6-di-t-butylphenyl)] dihydroxyaluminum, bis[phosphoric acid-2,2'-methylenebis(4,6-di-t-butylphenyl)] dihydroxyaluminum, tris[phosphoric acid-2,2'-methylenebis(4,6 -di-t-butylphenyl)] aluminum, sodium bis(4,6-di-t-butylphenyl)phosphate, benzoic acid metal salt such as sodium benzoate, aluminum p-t-butylbenzoate, 1,3:2,4-bis(O-benzylidene)sorbitol, 1,3:2,4-bis(O-ethylbenzylidene)sorbitol, 1,3:2,4-bis(O-bethylbenzylidene)sorbitol, 1,3-O-3,4-dimethylbenzylidene-2,4-O-benzylidenesorbitol, 1,3-O-benzylidene-2,4-O-3,4-dimethylbenzylidene sorbitol, 1,3:2,4-bis(O-3,4-dimethylbenzylidene) sorbitol, 1,3-O-p-chlorobenzylidene-2,4-O-3,4-dimethylbenzylidene sorbitol, 1,3-O-3,4-dimethylbenzylidene-2,4-O-p-chlorobenzylidene sorbitol, 1,3:2,4-bis(O-p-chlorobenzylidene)sorbitol and a mixture thereof.

Examples of the filler include calcium carbonate, silicate, glass fiber, asbestos, talc, kaoline, mica, barium sulfate, carbon black, carbon fiber, zeolite and a mixture thereof.

Among these additives above, phenol antioxidant, phosphorous antioxidant, ultraviolet absorber, hindered amine photostabilizer, peroxide scaveneger and neutralizing agent are preferably used.

Examples of the particularly preferred phenol antioxidant include the following compounds, and they may be used in combination of the two or more:

2,6-di-t-butyl-4-methylphenol, 2,4,6-tri-t-butylphenol, 2,4-dioctylthiomethyl-6-methylphenol, 2,2'-thiobis(6-t-butylphenol), 4,4'-thiobis(3-methyl-6-t-butylphenol), 2,2'-methylenebis(4-methyl-6-t-butylphenol), 2,2'-methylenebis[4-ethyl-6-t-butylphenol), 2,2'-methylenebis(4-ethyl-6-(α-methylcyclohexyl)phenol], 2,2'-methylenebis(4-methyl-6-cyclohexylphenol), 2,2'-methylenebis(4,6-di-t-butylphenol), 2,2'-ethylidenebis (4,6-di-t-butylphenol), 4,4'-methylenebis(6-t-butyl-2-methylphenol),4,4'-methylenebis(2,6-di-t-butylphenol), 4,4'-mbutylidenebis(3-methyl-6-t-butylphenol), 1,1'-bis(4-hydroxyphenyl)cyclohexane, 1,1-bis(5-t-butyl-4-hydroxy-2-methylphenyl)butane, 1,1,3-tris(5-t-butyl-4-hydroxy-2-methylphenyl)butane, ethylene glycol, bis[3,3-bis-3'-t-butyl-4'-hydroxyphenyl)butyrate], 2-t-butyl-6-(3'-t-butyl-5'-methyl-2'-hydroxybenzyl)-4-methylphenyl acrylate, 2,4-di-t-pentyl-6-[1-(2-hydroxy-3,5-di-t-pentylphenyl) ethyl]phenyl acrylate, 2,4,6-tris(3,5-di-t-butyl-4-phneoxy)-1,3,5-triazine, tris(4-t-butyl-3-hydroxy-2,6-dimethylbenzyl)isocyanurate, tris(3,5-di-t-butyl-4-hydroxybenzyl)isocyanurate, tris[2-(3',5'-di-t-butyl-4'-hydroxycinnamoyloxy)ethyl)isocyanurate, diethyl-3,5-di-t-butyl-4-hydroxybenzyl phosphonate, di-n-octadecyl-3,5-di-t-butyl-4-hydroxybenzyl phosphonate, calcium salt of 3,5-di-t- butyl-4-hydroxybenzylphosphonic acid monoester, n-octadecyl 3-(3,5-di-t-butyl-4-hydroxyphenyl)propionate, neopentanetetrayltetrakis(3,5-di-t-butyl-4-hydroxycinnamate), thiodiethylenebis(3,5-di-t-butyl-4-hydroxycinnamate), 1,3,5-trimethyl-2,4,6-tris(3,5-di-t-butyl-4-hydroxybenzyl)benzene, 3,6-dioxaoctamethylenebis(3,5-di-t-butyl-4-hydroxycinnamate), hexamethylenebis(3,5-di-t-butyl-4-hydroxycinnamate), triethylene glycol bis(5-t-butyll-4-hydroxy-3 -methylcinnamate),3,9-bis[2-(3-(3-t-butyl-4-hydroxy-5-methylphenyl)propionyloxy)-1,1-dimethylethyl]-2,4,8,10-tetraoxaspiro [5.5] undecane, N,N'-bis[3-(3',5'-di-t-butyl-4'-hydroxyphenyl) propionyl]hydrazine and N,N'-bis[3-(3',5'-di-t-butyl-4'-hydroxyphenyl)propionyl]hexamethylenediamine.

Examples of the particularly preferred phosphorous antioxidant include the followings, and they may be used in combination of the two or more:

tris(nonylphenyl)phosphite, tris(2,4-di-t-butylphenyl) phosphite, distearyl pentaerythritol diphosphite, bis(2, 4-di-t-butylphenyl)pentaerythritol diphosphite, bis(2,4-di-t-butyl-6-methylphenyl)pentaerythritol diphosphite, bis(2,6-di-t-butyl-4-methylphenyl)pentaerythritol diphosphite, tetrakis(2,4-di-t-butylphenyl)-4,4'-diphenylenediphosphite, 2,2'-methylenebis(4,6-di-t-butylphenyl) 2-ethylhexyl phosphite, 2,2'-ethylidenebis (4,6-di-t-butylphenyl) fluorophosphite, bis(2,4-di-t-butyl-6-methylphenyl) ethylphosphite, 2-(2,4,6-tri-t-butylphenyl)-5-ethyl-5-butyl-1,3,2-oxaphospholinane and 2,2',2"-nitrilo[triethyl-tris(3,3',5,5'-tetra-t-butyl-1, 1'-biphenyl-2,2'-diyl)phosphite.

Examples of the particularly preferred ultraviolet absorber include the followings, and two or more kinds of them can be used.

phenyl salicylate, 4-t-butylphenyl salicylate, 2,4-di-t-butylphenyl 3',5'-di-t-butyl-4'-hydroxybenzoate, 4-t-octylphenyl salycilate, 2,4-dihydroxybenzophenone, 2-hydroxy-4-methoxybenzophenone, 2-hydroxy-4-octoxybenzophenone, 2,2'-dihydroxy-4-methoxybenzophenone, bis(5-benzoyl-4-hydroxy-2-methoxyphenyl)methane, 2,2',4,4"-tetrahydroxybenzophenone, 2-(2-hydroxy-5-methylphenyl) benzotriazole, 2-(3',5'-di-t-butyl-2'-hydroxyphenyl) benzotriazole, 2-(5'-t-butyl-2'-hydroxyphenyl) benzotriazole, 2-(2'-hydroxy-5'-t-octylphenyl)benzotriazole, 2-(3-t-butyl-2-hydroxy-5-methylphenyl)-5-chlorobenzotriazole, 2-(3'-s-butyl-2'-hydroxy-5'-t-butylphenyl)benzotriazole, 2-(2'-hydroxy-4'-octyloxyphenyl)benzotriazole, 2-(3',5'-di-t-amyl-2'-hydroxyphenyl)benzotriazole and 2-[2'-hydroxy-3',5 '-bis(α, α-dimethylbenzyl)phenyl]-2H-benzotriazole.

Examples of the particularly preferred photostabilizer include the followings, and two or more kinds of them can be used.

bis(2,2,6,6-tetramethyl-4-piperidyl)sebacate, bis(1,2,2,6, 6-pentamethyl-4-piperidyl)sebacate, bis(N-octoxy-2,2,6,6-pentamethyl-4-piperidyl)sebacate, bis(N-octoxy-2,2,6,6-pentamethyl-4-piperidyl)sebacate, bis(N-benzyloxy-2,2,6, 6-tetarmethyl-4-piperidyl)sebacate, bis(N-cyclohexyloxy-2, 2,6,6-tetramethyl-4-piperidyl)sebacate, bis(1,2,2,6,6-pentamethyl-4-piperidyl) 2-(3,5-di-t-butyl-4-hydroxybenzyl)-2-butylmalonate, bis(1-acryloyl-2,2,6,6-tetramethyl-4-piperidyl) 2,2-bis(3,5-di-t-butyl-4-hydroxybenzyl)-2-butylmalonate, bis(2,2,6,6-tetramethyl-4-piperidyl)succinate, 2,2,6,6-tetramethyl-4-piperidyl methacrylate, 4-[3-(3,5-di-t-butyl-4-hydroxyphenyl) propionyloxy)-1-[2-(3-(3,5-di-t-butyl-4-hydroxyphenyl) propionyloxv)ethyl]-2,2,6,6 -tetramethylpiperidine, 2-methyl-2-(2,2,6,6-tetramethyl-4-piperidyl)amino-N-(2,2, 6,6-tetarmethyl-4-piperidyl)propionamide, tetrakis(2,2,6,6- tetramethyl-4-piperidyl) 1,2,3,4-butanetetracarboxylate. tetrakis(1,2,6,6-pentamethyl-4-piperidyl) 1,2,3,4-butanetetracarboxylate, mixed esterified Droduct of 1,2,3,4-butanetetracarboxylic acid and 1,2,2,6,6-pentamethyl-4-piperidinol and 1-tridecanol, mixed esterified product of 1,2,3,4-butanetetracarboxylic acid and 2,2,6,6-tetramethyl-4-piperidinol and 1-tridecanol, mixed esterified product of 1,2,3,4-tetracarboxylic acid and 1,2,2,6,6-pentamethyl-4-piperidinol and 3,9-bis(2-hydroxy-1,1-dimethylethyl)-2,4,8,10-tetraoxaspiro[5.5]undecane, mixed esterified product of 1,2,3,4-butanetetracarboxylic acid and 2,2,6,6-tetarmethyl-4-piperidinol and 3,9-bis(2-hydroxy-1,1-dimethylethyl)-2,4,8,10-tetraoxaspiro[5.5]undecane, polycondensate of dimethyl succinate and 1-(2-hydroxyethyl)-4-hydroxy-2,2,6,6-tetramethylpiperidine, poly[(6-morpholino-1,3,5-triazin-2,4-diyl)((2,2,6,6-tetramethyl-4-piperidyl)imino) hexamethylene ((2,2,6,6-tetramethyl-4-piperidyl)imino)] and poly[(6-(1,1,3,3-tetramethylbutyl)-1,3,5-triazin-2,4-diyl ((2,2,6,6-tetramethyl-4-piperidyl)imino)hexamethylene ((2,2,6,6-tetramethyl-4-piperidyl)imino)].

For formulating the organic phosphorous compounds (I) and optionally used other additives in the organic material, known all methods and devices for obtaining a homogeneous mixture can be used. For example, when the organic material is a solid polymer, the organic phosphorous compounds (I) and other additives can be directly dry-blended in the solid polymer, or the organic phosphorous compounds (I) and other additives can also be formulated in the solid polymer in the form of a master-batch. When the organic material is a liquid polymer, the organic phosphorous compounds (I) and other additives can be formulated in the polymer solution during or immediately after polymerization in the form of a solution or a dispersion. On the other hand, when the organic material is a liquid such as oil, the organic phosphorous compounds (I) and other additives can also be dissolved by direct addition, or the organic phosphorous compounds (I) and other additives can also be added in the form of a solution or dispersion in a liquid medium.

The organic phosphorous compounds (I) of the present invention have excellent performance as a stabilizer for various organic materials such as thermoplastic resin (e.g. polyolefin, etc.), and the organic material containing this compound is stable to heat and oxidization on their production, processing and use. Therefore, high-quality product can be obtained.

The following Examples further illustrate the present invention in detail but are not to be construed to limit the scope thereof.

EXAMPLE 1

Production of N-[3-(3-t-butyl-4-hydroxy-5-methylphenyl)propionyl]-N'-(2,4,8,10-tetra-t-butyl-dibenzo[d,f][1,3,2]dioxaphosphepin-6-ylpiperazine (Compound 1)

In a flask equipped with a thermometer, a stirrer and a cooling condenser, 3,3',5,5'-tetra-t-butylbiphenyl-2,2'-diol (20.5 g) and toluene (150 ml) were charged under a nitrogen flow. After phosphorous trichloride (6.8 g) was added under stirring, triethylamine (10.5 g) was added further and the mixture was maintained at 80° C. for 4 hours.

After cooling the mixture to room temperature, toluene (100 ml) and N-[3-(3-t-butyl-4-hydroxyl-5-methylphenyl) propionyl]piperazine (15.2 g) were added thereto. Then, triethylamine (5.2 g) was added thereto, followed by maintaining the mixture at 80° C. for 5 hours.

After cooling the resultant mixture to room temperature, the formed hydrochloride salt of triethylamine was filtered and washed. After the filtrate was concentrated, the residue was purified by silica gel chromatography to obtain 13.7 g of a white crystal.

Mass spectrometric analysis (FD-MS): m/z 743

Melting point: 110° C.

$^1$H-NMR (CDCl$_3$)

1.34 (s, 18H), 1.38 (s, 9H), 1.45 (s, 18H), 2.20 (s, 3H), 2.51 (t, 2H), 2.81 (t, 2H), 3.23 (m, 4H), 3.48 (m, 4H), 4.67 (s, 1H), 6.81 (d, 1H), 6.92 (d, 1H), 7.15 (d, 2H), 7.39 (d, 2H)

$^{31}$P-NMR (CDCl$_3$)

142.5 ppm (s)

EXAMPLE 2

Production of N-[3-(3-t-butyl-4-hydroxy-5-methylphenyl)propionyl]-N'-(2,4,8,10-tetra-t-butyl-12H-methyl-dibenzo[d,g][1,3,2]dioxaphosphosine-6 yl)piperazine(Compound 2)

According to the same manner as in Example 1 except for using 2,2'-ethylidenebis(4,6-di-t-pentylphenol) (21.6 g) in place of 3,3',5,5'-tetra-t-butylbiphenyl-2,2'-diol, 25.3 g of a white crystal was obtained.

Mass spectrometr c analysis (FD-MS): m/z 770

Melting point: 195° C.

$^1$H-NMR (CDCl$_3$)

1.29 (s, 18H), 1.39 (s, 18H), 1.42 (s, 9H), 1.58 (d, 3H), 2.24 (s, 3H), 2.64 (t, 2H), 2.91 (t, 2H), 3.40 (m, 4H), 3.50 (m, 4H), 4.73 (s, 1H), 4.87 (q, 1H), 6.88 (d, IH), 7.00 (d, 1H), 7.18 (d, 2H), 7.39 (d, 2H)

$^{31}$P-NMR (CDCl$_3$)

137.4 ppm (s)

EXAMPLE 3

Thermal Stabilization Test of Linear Low-Density Polyethylene

[Formulation]

| | |
|---|---|
| Unstabilized linear low-density polyethylene | 100 Parts by weight |
| Hydrotalcite | 0.1 Parts by weight |
| Test compound | 0.15 Parts by weight |

C-1: compound 1 (produced in Example 1)

C-2: compound 2 (produced in Example 2)

P-1: N,N'-bis(2,4,8,10-tetra-t-butyl-dibenzo[d,f][1,3,2] dioxaphosphepin-6-yl)piperazine Using a 30 mm ø single-screw extruder, the above formulation was repelletized at 250° C. Using a laboplasto mill, the resulting pellets were kneaded at 240° C., 100 rpm under a nitrogen atmosphere. The time required for the torque value to become maximum (gel build-up time) was measured. The results are shown in Table 1. The longer the gel build-up time, the more the crosslinking on kneading is inhibited, which indicates excellent processing stability.

Furthermore, the resulting pellets were kneaded at 230° C., 10 rpm, for 5 minutes using a laboplasto mill, and then pressed at 250° C. to form a sheet. The YI (yellow index) value of this sheet was measured. The results are shown in Table 1. The evaluation criteria are as follows.

◯: YI value =0–5

Δ: YI value =5–10
x: YI value >10

TABLE 1

|  | Example | | Comparative Example | |
|---|---|---|---|---|
|  | 1 | 2 | 1 | 2 |
| Test compound | C-1 | C-2 | — | P-1 |
| Processing stability | 18.0 | 17.5 | 5.0 | 6.0 |
| Hue | ○ | ○ | — | × |

EXAMPLE 4

Thermal Stability Test of Nylon

[Formulation]

| Unstabilized nylon 6 | 100 Parts by weight |
| Test stabilizer | 0.5 Parts by weight |

C-1: compound 1 (produced in Example 1)
C-2: compound 2 (produced in Example 2)
P-1: N,N'-bis(2,4,8,10-tetra-t-butyl-dibenzo[d,f][1,3,2]dioxaphosphepin-6-yl)piperazine The above formulating materials were kneaded by dry blending and then kneaded at 300° C., 80 rpm for 5 minutes using a laboplasto mill. The torque value after 5 minutes is shown in Table 3. The higher the torque value after 5 minutes, the better the processing stability becomes, because nylon 6 is decomposed by deterioration to reduce the torque value.

TABLE 2

|  | Example | | Comparative Example | |
|---|---|---|---|---|
|  | 1 | 2 | 1 | 2 |
| Test compound | C-1 | C-2 | — | P-1 |
| Torque value (kgf) | 52 | 48 | 22 | 30 |

What is claimed is:

1. An organic phosphorous compound represented by the following formula (I):

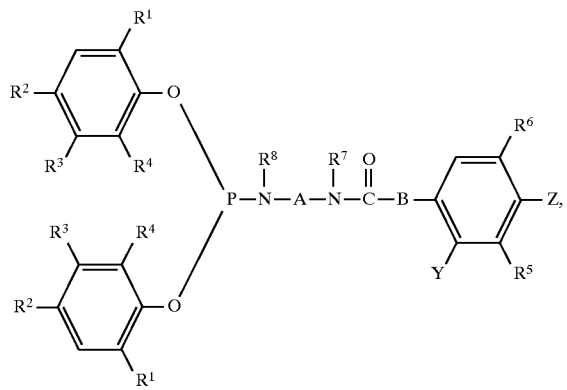

wherein $R^1$, $R^2$, $R^5$ and $R^6$ independently represent a hydrogen atom, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms or a phenyl group; $R^3$ represents a hydrogen atom or an alkyl group having 1 to 8 carbon atoms; $R^4$ represents a hydrogen atom, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms or a phenyl group, or the two $R^4$ may be combined with each other to form a direct bond, a sulfur bond (—S—), or a methylene group which is optionally substituted with alkyl having 1 to 8 carbon atoms or cycloalkyl having 5 to 8 carbon atoms; $R^7$ and $R^8$ independently represent a hydrogen atom or an alkyl group having 1 to 8 carbon atoms, or $R^7$ and $R^8$ may be combined with each other to form an alkylene group having 2 to 4 carbon atoms; A represents an alkylene group having 2 to 8 carbon atoms; B represents a direct bond or an alkylene group having 1 to 8 carbon atoms; and one of Y and Z represents a hydroxyl group, an alkoxy group having 1 to 8 carbon atoms or an aralkyloxy group having 7 to 12 carbon atoms, and the other one represents a hydrogen atom or an alkyl group having 1 to 8 carbon atoms.

2. A process for producing the organic phosphorous compound according to claim 1, which comprises reacting a phenol or a bisphenol represented by the following formula (II):

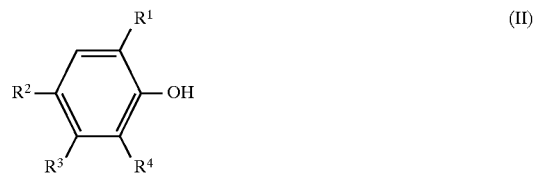

wherein $R^1$, $R^2$, $R^3$ and $R^4$ are as defined in claim 1, phosphorous trihalide, and an amine compound represented by the following formula (III):

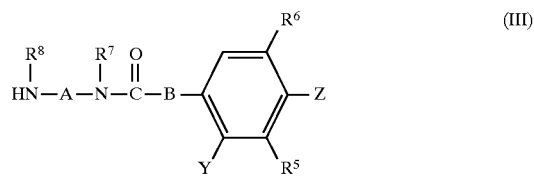

wherein $R^5$, $R^6$, $R^7$, $R^8$, A, B, Y and Z are as defined in Claim 1.

3. A stabilizer for an organic material which comprises the organic phosphorous compound according to claim 1.

4. A method for stabilizing an organic material which comprises adding the organic phosphorous compound according to claim 1 to the organic material.

5. The method according to claim 4, wherein the organic material is a thermoplastic resin.

6. The method according to claim 5, wherein the thermoplastic resin is a polyolefin, polyamide, polyethylene terephthalate, polybutylene terephthalate or polycarbonate.

7. A composition which comprises an organic phosphorous compound according to claim 1 and an organic material.

8. The composition according to claim 7, wherein the organic material is a thermoplastic resin.

9. The composition according to claim 8, wherein the thermoplastic resin is a polyolefin, polyamide, polyethylene terephthalate, polybutylene terephthalate or polycarbonate.

10. The method according to claim 5, wherein the thermoplastic resin comprises a polyolefin resin.

11. The method according to claim 5, wherein the thermoplastic resin comprises at least one selected from the group consisting of polyamide, polyethylene terephthalate, polybutylene terephthalate and polycarbonate.

12. The composition according to claim 8, wherein the thermoplastic resin comprises a polyolefin resin.

13. The composition according to claim 8, wherein the thermoplastic resin comprises at least one selected from the group consisting of polyamide, polyethylene terephthalate, polybutylene terephthalate and polycarbonate.

* * * * *